United States Patent [19]
Cornell

[11] Patent Number: 4,957,637
[45] Date of Patent: Sep. 18, 1990

[54] SERUM SEPARATOR SYSTEM FOR CENTRIFUGE WITH PIERCABLE MEMBRANE

[75] Inventor: William D. Cornell, Ballwin, Mo.

[73] Assignee: Sherwood Medical Company, St. Louis, Mo.

[21] Appl. No.: 197,753

[22] Filed: May 23, 1988

[51] Int. Cl.⁵ .................. B01D 33/00; B01D 21/26
[52] U.S. Cl. ..................... 210/782; 210/359; 210/472; 210/516; 210/518; 422/101; 604/184; 604/190; 604/191; 604/237; 604/406; 604/411; 604/89; 494/37
[58] Field of Search ............... 210/359, 514, 516, 518, 210/472, 782; 422/101; 604/89, 90, 184, 190, 191, 237, 406, 411; 494/37

[56] References Cited
U.S. PATENT DOCUMENTS

| | | | |
|---|---|---|---|
| 3,661,265 | 5/1972 | Greenspan | 210/359 |
| 3,706,305 | 12/1972 | Berger et al. | 604/148 |
| 3,894,952 | 7/1975 | Ayres | 210/516 |
| 3,897,337 | 7/1975 | Ayres | 210/359 |
| 3,931,010 | 1/1976 | Ayres et al. | 210/359 |
| 4,035,150 | 7/1977 | Jaffe | 210/359 |
| 4,057,499 | 11/1977 | Buono | 210/359 |

Primary Examiner—W. Gary Jones
Assistant Examiner—Cynthia L. Nessler
Attorney, Agent, or Firm—Andrew J. Beck; Montgomery W. Smith; Charles Smith

[57] ABSTRACT

A device for separating and isolating heavier components from lighter components of blood mixtures after centrifugal separation, comprising a barrel for holding the blood mixture having slidably positioned therein an inner container for containing the lighter components, a one-way valve responsive to movement of the container within the barrel (a) for controlling the flow of the lighter components into the container, (b) for preventing the lighter components from re-entering the barrel from the container, and (c) for creating a vacuum to assist in drawing the blood mixture to be separated into the barrel, and a filter for filtering the lighter components during their entry into the inner container. The inner container includes an opening for access to the separated and isolated lighter components.

14 Claims, 2 Drawing Sheets

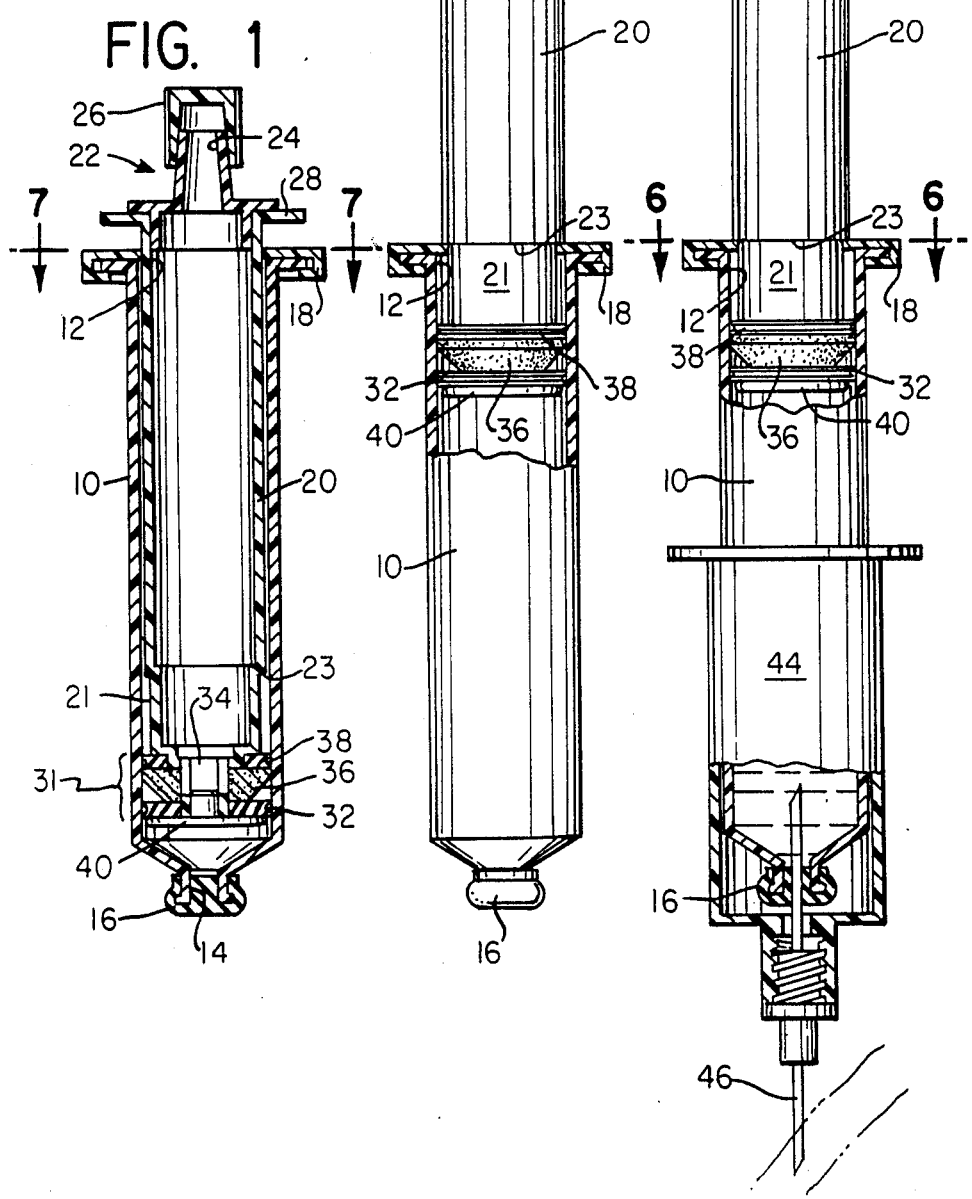

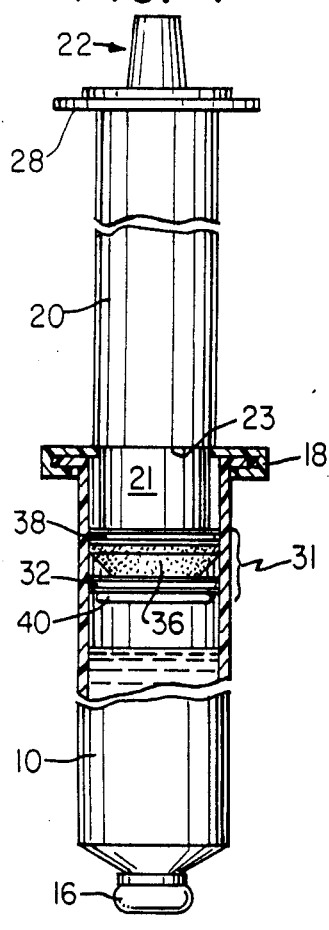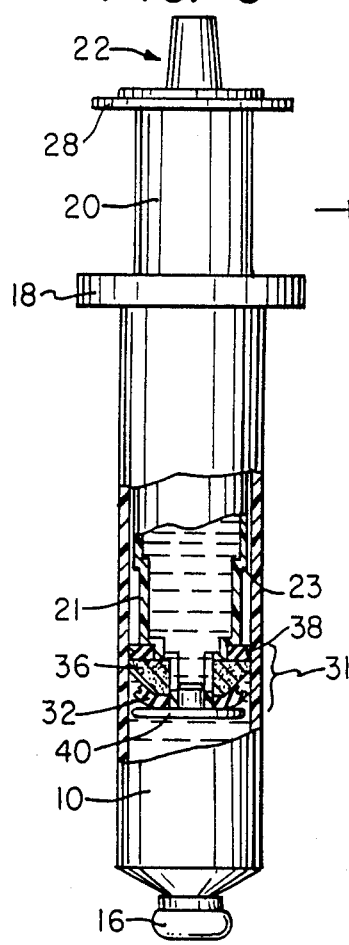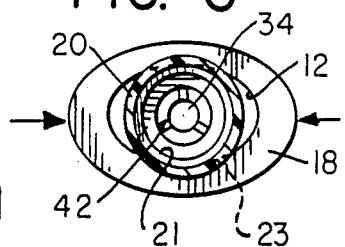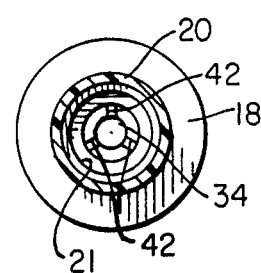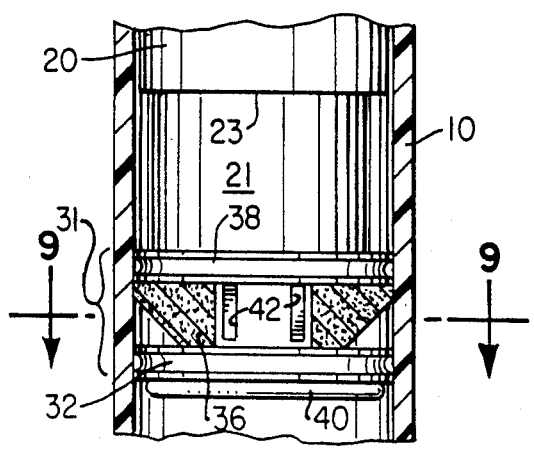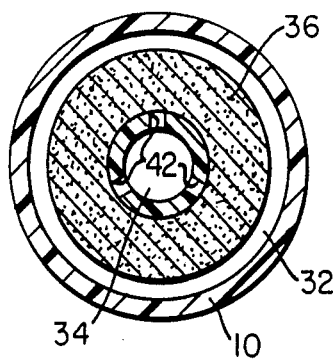

SERUM SEPARATOR SYSTEM FOR CENTRIFUGE WITH PIERCABLE MEMBRANE

BACKGROUND OF THE INVENTION

The invention relates to the separation of the heavy components of a blood sample (called the heavy phase), i.e., white cells, red cells and platelets from the lighter components (called the light phase), i.e., serum and plasma of blood.

Such separation is typically performed by centrifuging the blood sample so that the heavier components are forced to one end of a container and the lighter components separate to the other.

After the separation, the two phases can be physically separated into isolated containers and tested individually. If this physical separation is not made or is not readily made, the separate phases of the blood sample will become contaminated, for example, as the red blood cells begin to liberate potassium. This and other contaminants could interfere with the blood sample testing.

The physical separation of the two phases of the blood sample can be achieved during the initial centrifuging step of phase separation or shortly thereafter through the use of a mechanical separator, of which there are many. U.S. Pat. Nos. 4,492,634, 3,508,653, 4,230,584, 3,960,727, 3,972,812, 3,945,928, 4,202,769, and 4,001,122 all disclose apparatus which physically separate the two specific gravity differentiated phases of a blood sample during or shortly after the centrifuging process.

Such blood separation apparatus usually includes a container similar in shape to a test tube, and an insertable barrier plate usually housing a one-way valve and filter material and providing an effective seal along the inside wall of the container. This barrier plate can be made to have a certain specific gravity which is greater than the light phase of the blood such that during the centrifuge phase separation, the barrier plate will move through the lighter phase until it reaches a level corresponding to its specific gravity. The barrier plate can also be manually inserted past the light phase to the phase barrier, after centrifuging. This barrier plate, once in place, defines two isolated chambers in the main container, one for each phase.

SUMMARY OF THE INVENTION

The primary object of the present invention is to provide an improved, compact device that may be used to collect a blood sample from a patient, separate the blood sample into its light and heavy phases, and maintain phase separation such that portions of either phase may be removed without contamination to the other.

Another objective of the present invention is to provide an improved blood plasma separator that simplifies the procedure required for the separation and containment of a blood sample.

It is another objective of the present invention to provide an improved blood plasma separator which utilizes a plunger-type handle to create the necessary vacuum for drawing a blood sample directly from a patient and for containing the lighter phase of the blood sample after separation.

It is a further objective of this invention to provide a novel locking means which locks the plunger-type handle in place until its movement is required.

BRIEF DESCRIPTION OF THE DRAWINGS

FIG. 1 is a longitudinal section of a plasma separator of the present invention with the plunger-type handle located within the barrel;

FIG. 2 is a longitudinal section view of the present invention with the handle locked in a position external to the barrel;

FIG. 3 shows the plasma separator of FIG. 2 inserted into a conventional hypodermic needle housing, drawing blood from the patient;

FIG. 4 shows the present plasma separator with the blood sample separated, but not isolated;

FIG. 5 is a side view of the present plasma separator showing the handle being lowered into the barrel and the seal valve deflected into an open position.

FIG. 6 shows a top view of the handle locking mechanism in the locked position;

FIG. 7 shows a top view of the present handle locking mechanism in the unlocked position;

FIG. 8 shows a side view of the plunger of the present invention;

FIG. 9 shows a section view of the plunger shown in FIG. 8; and

FIG. 10 shows the upper portion of the barrel with a vacuum release passageway.

DETAILED DESCRIPTION OF THE PREFERRED EMBODIMENT

Referring to FIG. 1, there is shown a cylindrical barrel 10 made from a conventional semi-rigid thermoplastic material, having a lower circular end which is sharply tapered in diameter, like a funnel, to a smaller circular opening 14. An upper end 12 is open to receive a mating cylindrical container 20 described below. The smaller opening 14 is covered and sealed by a conventional elastic membrane 16, such as natural rubber, so that a hypodermic needle can pierce the membrane 16 and provide fluid access to the container 10. The outer diameter of the barrel 10 is slightly less than the inner diameter of a conventional syringe barrel housing 44, which includes the necessary needle 46 to pierce the membrane 16. The barrel 10 is received by the housing 44 and the needle 46 pierces the membrane 16.

Attached around the upper end 12 of barrel 10 is an oval-shaped flange 18 which preferably is made from the same semi-rigid thermoplastic as the barrel 10. This flange 18 extends outward from the edge of the barrel 10 and is in partial overlapping relation to the circular shaped end 12 of the barrel 10. The flange 18 can be deformed from the oval-shaped by pinching together the opposing edges of greatest diameter into a circular shape which is substantially similar in diameter to the circular shape of the upper end 12 of the barrel 10.

A cylindrically shaped container 20 is made from semi-rigid thermoplastic material and has an outer diameter which is slightly less than the inside diameter of the barrel 10 such that the container 20 can easily slide out from and into the barrel 10 in a telescoping fashion, similar to the operation of a conventional syringe. The container 20 is also greater in length than the barrel 10 so that when the container 20 is completely inserted to a lower position into the barrel 10 through the opening 12, as shown in FIG. 1, a portion of an upper end 22 of the container 20 remains above the oval-shaped flange 18 of the barrel 10. The upper end 22 of container 20 is circular in cross section and is tapered down to an opening 24. The opening 24 allows the operator access to the light phase of the blood sample which will eventually, after separation and isolation be contained in the container 20. The opening 24 can be sealed by a removable cap 26.

A second flange 28, circular in shape is located around the upper end 22 of the container 20 so that when the container 20 is completely inserted into the barrel 10, the second flange 28 remains above the upper end 12 of the barrel 10 and provides a support to assist the operator in positioning the container 20 within the barrel 10.

The container 20 has a lower recessed portion 21 which is concentrically smaller in diameter than the outer diameter of the container 20 and greater in diameter than the smaller diameter of the oval flange 18. This recessed portion 21 defines a step 23 around the side of the container 20 which matingly corresponds to the oval flange 18. As the container 20 is drawn from the barrel 10, as shown fully drawn to an upper position in FIG. 2, the oval flange portion of smaller diameter slides along the outer surface of the container 20, and, owing to the spring bias of the oval flange 18, locks into the recessed portion 21 when the step 23 of the container 20 aligns with the top edges of the oval flange 18.

Attached to the lower end of the recessed portion 21 of the container 20 is an isolating/filtration mechanism which includes a filter region 31 which houses a flexible valve disc 32, a fluid passage 34, and a filter ring 36, a plunger sealing ring 38, and a valve disc support 40.

The plunger sealing ring 38 is fixed to the edges of the lower end of the recessed portion 21 and protrudes radially outward having an outer diameter which is similar to the inside diameter of the barrel 10 such that the ring 38 creates an air/liquid tight seal against the inside walls of the barrel 10. This seal helps prevent contamination of the blood sample in the barrel 10 and also permits a vacuum to be created when the container 20 is drawn to the upper end 12 from within the outer barrel 10.

The lower end of the recessed portion 21 of the container 20 is further recessed, thereby defining the fluid passage 34. The fluid passage 34 provides fluid communication between the barrel 10 and the container 20.

The valve disc support 40 is a circular plate attached perpendicularly to the bottom of the fluid passage 34 and has an outer diameter which is substantially similar to the outer diameter of the container 20. This valve disc support 40 seals the bottom of the fluid passage 34 such that blood located in the barrel 10 can not pass directly through the fluid passage 34 to the container 20.

The filter region 31 is defined by the area below the plunger seal 38 and above the valve disc support plate 40.

The valve disc 32 is made from elastomeric flexible material such as rubber and has an outer diameter which is substantially similar to the outer diameter of the plunger sealing ring 38 so that under certain conditions, with the support of the valve disc support plate 40, described below, the valve disc can permit the creation of a vacuum within the container 20 to aid in withdrawal of blood from a patient and can prevent the return flow of the lighter phase from the container 20 to the barrel 10. This valve disc lies within the filter region 31, on top of the valve disc support plate 40 and around the fluid passage 34.

The filter ring 36 is similar in shape to an inverted truncated cone and surrounds the central fluid passage 34. The filter ring 36 is positioned in the filter region 31 with the filter end of greatest diameter butting the plunger sealing ring 38 and the cone shape beveling inwardly and facing downward, thereby resting on a circularly shaped inner portion of the top of the valve disc 32. The truncated cone shaped filter ring 36 has a smaller diameter than the diameter of the valve disc support plate 40 which allows the outer edges of the flexible valve disc to bend upwardly during downward plunger movement. During such plunger movement, the seal created by the valve disc and the inner walls of the barrel 10 is broken and fluid from the barrel 10 may pass into the filter region 31.

The filter 36 assists in removing any heavy phase portions that have mixed with the light phase shortly after the centrifuging process due to turbulence caused by syringe handling. The filter also removes fiber from the light phase which will accumulate if the separated sample is left sitting, unfiltered for any great length of time. The filter 36 is made from a conventional porous material whose porosity range is precalculated in a testing laboratory so as to filtrate the light phase properly.

Slots 42 are provided in the wall of the fluid passage 34 which allows the lighter phase of the blood sample to pass from the filter region 31 to the container 20.

In operation, the container 20 is drawn from the inside of the barrel 10 with the removable cap 26 positioned such that the upper opening 24 of the container 20 is sealed. The container 20 is drawn until the oval flange 18, which is spring biased inwardly, locks into the recessed portion 21 of the container 20. The plunger seal ring 38 will prevent outside air from entering the barrel 10. While the container 20 is being removed from the barrel 10 the edges of the valve disc 32 will be forced downward against the valve support plate 40 and therefore will also form an air seal against the inner walls of the barrel 10 and will cause a vacuum to be created within the barrel. The assembly is then inserted into a conventional syringe barrel holder 44. The holder 44 includes a needle, one end of which is positioned in the bloodstream of the patient and the other end is positioned inside the holder such that it pierces the elastic membrane 16.

When the needle 46 pierces the membrane 16, blood from the patient will enter the barrel 10, assisted by the vacuum. This is shown in FIG. 3.

The assembly with the blood sample in the barrel 10 and the inner container 20 locked in the upper position, as shown in FIG. 4, is then removed from the syringe holder 44 and placed in a conventional centrifuge of the type which can accommodate the fully extended container 20.

After the centrifuging, the blood will have separated into the two primary phases, a heavy phase located closer to the membrane 16 and a lighter phase located closer to the container 20.

With the removable cap 26 removed, the container 20 is then unlocked from its fully extended position by the operator pinching together the opposing sides of the oval flange having the greatest diameter, thereby forcing the oval flange into a shape which is substantially similar to the shape of the container 20, as is shown in FIGS. 6 and 7. This allows the locking step 23 to move downwardly with the container 20 into the barrel 10 and into the lighter of the two phases of the separated blood sample.

The light phase of the blood sample passes between the outer edges of the valve disc 32, which are curving upwardly, and the inner walls of the barrel 10, as the plunger is moved further into the light phase by the operator. The light phase is then forced through the filter material of the filter ring 36 and into the fluid passage 34 via the slots 42. The filtered light phase is then stored in the container 20. Any pressure developing in the container while the light phase enters is immediately released through the upper opening 24, uncovered by cap 26. The operator visually positions the valve disc through the light phase until it lies just above the phase interface, physically isolating the lighter phase from the heavier phase. The pressure exerted onto the top portion of the valve disc by the collected light phase in the container 20 will reinforce the valve seal and will prevent the light phase from re-entering the barrel 10.

The separated and filtered light phase can be immediately poured out of the container 20 through upper hole 24 by removing cap 26. The container 20 can than be removed from the barrel 10 to provide access to the heavy phase. However, when removing the container 20 from the barrel 10 a vacuum will form above the surface of the heavy blood portion of the sample and unless this vacuum reaches equilibrium (atmospheric pressure) slowly and in a controlled manner any sudden inrush of air flow into the barrel 10 can generate an aerosol of the blood sample which can cause contamination of the local environment resulting in a health hazard to medical personnel. Passageway 48 shown in FIG. 10 is disposed within the inside wall of the barrel 10 along its upper end. This passageway 48 connects the chamber of barrel 10 with the pressure outside the syringe barrel (usually atmospheric) when the edge of the flexible valve disc 32 passes it during extreme upward movement of the container 20. The passageway 48 therefore has a first end in fluid communication with the inside of the barrel and a second end in fluid communication with the outside of the device. The resulting communication between the barrel chamber and the atmosphere equilibrates the negative pressure in a controlled and slow manner, thereby avoiding any disturbing air turbulence within the barrel chamber. Passageway 48 is not located low enough along the barrel to affect the beneficial vacuum used during the drawing-of-blood procedure.

What is claimed is:

1. An assembly to be used in connection with a centrifuge, for separating and isolating lighter components from heavier components of blood mixtures, comprising:

an elongated barrel for holding a blood specimen, said barrel being open at its upper end and including a piercable membrane across its lower end, said membrane being adapted to be selectively pierced by a needle such that a blood specimen drawn through said needle may enter into said barrel;

a mating container positioned in said barrel and slidable therein as a plunger, said container including a fluid opening at both its lower end and its upper end;

means for selectively sealing said lower opening of said container depending on the direction of container movement in said barrel, said sealing means becoming closed when said container is pulled upwardly in the barrel such that a vacuum is created in said barrel solely by relative movement of said barrel and said container, said sealing means becoming open when said container is pushed downwardly in the barrel allowing liquid to pass from said barrel, through said lower opening and into said container; and filtration means located at the lower end of said container for permitting the passage of soluble components of said blood specimen from said barrel to said container, but preventing passage of insoluble components when the container is pushed into the barrel with said upper opening of said container open.

2. The assembly according to claim 1 wherein said upper opening of said container is sealable by a removable airtight cap.

3. The assembly according to claim 1 wherein said barrel and said mating container are circular in cross section.

4. The assembly according to claim 1 wherein the barrel has a means defining a passageway having a first end in fluid communication with the inside of said barrel and a second end in fluid communication with the outside of said assembly when said sealing means passes said first end during extreme upward movement of said container, said first end of said passageway being located along said barrel such that said vacuum created during upward movement is equilibrated with the pressure outside said assembly just before said container is separated from said barrel, thus avoiding air turbulence within said barrel.

5. The assembly according to claim 1 wherein said sealing means comprises a one-way valve for allowing liquid from said barrel to pass through said lower opening of said container when the container is pushed into said barrel and for preventing flow of liquid from said container to said barrel when the container is pulled from said barrel or said barrel is stationary.

6. The assembly according to claim 5 wherein said one way valve further comprises a plate of flexible material which is rigidly supported on one side and positioned within said barrel such that said plate bends towards the unsupported side when the container is pushed into the barrel, thereby allowing liquid from said barrel to pass through said lower opening of said container, said plate remains against the rigid support when the container is pulled from the barrel forming a liquid tight seal between the container and the barrel which prevents liquid in the container from re-entering the barrel.

7. The assembly according to claim 5 wherein said one-way valve comprises:

an elastomeric sealing disc having a circumferential sealing edge and being substantially similar in shape to the cross-sectional shape of said barrel; and a rigid support plate attached to said container adjacent to said lower opening of said container and slidable therewith in said barrel, said support plate supporting said sealing disc and being substantially similar in shape to that of said sealing disc, said support plate and said sealing disc being located within said barrel such that when said container movement is upward relative to said barrel, said sealing edge frictionally contacts the inner walls of said barrel and forces downward against said support plate, thus preventing said flow of liquid between said barrel and said container, and when said container movement is downward relative to said barrel, said sealing edge rises owing to said frictional contact, thereby allowing said liquid from said barrel to enter said lower opening of said container.

8. The assembly according to claim 1, further comprising a locking means for locking said container in an upper position within said barrel, thereby preventing unintended movement of said container within said barrel during centrifuging.

9. The assembly according to claim 8 wherein said locking means comprises:
a locking means including a recessed step located around said container: and
a flexible oval-shaped flange located at said upper opening of said barrel, a portion of said oval flange positioned in an overlapping relationship with the path of said container within said barrel so that when said recessed step of said container aligns with said oval flange, said overlapping portion secures itself against said recessed step, thereby preventing movement of said container into said barrel, said oval-shaped flange transformable to a shape which is substantially similar to the cross section of said container, thereby disengaging said flange from said recessed step and allowing container movement within said barrel.

10. The assembly according to claim 1 further comprising means for equilibrating gaseous pressure within said barrel and gaseous pressure outside of said barrel just prior to separating said container from within said barrel, thus avoiding air turbulence within said barrel when said container is separated from within said barrel.

11. The assembly according to claim 10 wherein said means for equilibrating said gaseous pressures includes means defining a passageway disposed along said barrel, said passageway means being positioned such that said gaseous pressure in said barrel will equilibrate with said pressure outside of said barrel only during extreme upward movement of said container within said barrel.

12. An assembly to be used in connection with a centrifuge, for separating and isolating lighter components from heavier components of blood mixtures, comprising:
a first elongated barrel for holding a blood specimen, said barrel being open at its upper end and including a needle at its lower end for providing entry of said blood specimen;
a container positioned in said barrel and slidable therein as a plunger, said container including a fluid opening at both its lower end and its upper end;
means for selectively sealing said lower opening of said container depending on the direction of container movement in said barrel, said sealing means becoming closed when said container is pulled upwardly in the barrel such that a vacuum is created in said barrel, said sealing means becoming open when said container is pushed downwardly in the barrel allowing liquid to pass from said barrel, through said lower opening and into said container;
filtration means located at the lower end of said container for permitting the passage of soluble components of said blood specimen from said barrel to said container, but preventing passage of insoluble components when the container is pushed into the barrel with said upper opening of said container open; and
a locking means including a recessed step located around said container and a flexible oval-shaped flange located at said upper opening of said barrel, a portion of said oval flange positioned in an overlapping relationship with the path of said container within said barrel so that when said recessed step of said container aligns with said oval flange, said overlapping portion secures itself against said recessed step, thereby preventing movement of said container into said barrel, said oval-shaped flange transformable to a shape which is substantially similar to the cross section of said container, thereby disengaging said flange from said recessed step and allowing container movement within said barrel.

13. An assembly to be used in connection with a centrifuge, for separating and isolating lighter components from heavier components of blood mixtures, comprising:
a first elongated barrel for holding a blood specimen, said barrel being open at its upper end and including a needle at its lower end for providing entry of said blood specimen, said barrel having a means defining a passageway comprising a first end in fluid communication with the inside of said barrel and a second end in fluid communication with the outside of said assembly when said sealing means passes said first end during extreme upward movement of said container, said first end of said passageway being located along said barrel such that said vacuum created during upward movement of said container in said barrel is equilibrated with the pressure outside said assembly just before said container is separated from said barrel, thus avoiding air turbulence within said barrel;
a container positioned in said barrel and slidable therein as a plunger, said container including a fluid opening at both its lower end and its upper end;
means for selectively sealing said lower opening of said container depending on the direction of container movement in said barrel, said sealing means becoming closed when said container is pulled upwardly in the barrel such that a vacuum is created in said barrel, said sealing means becoming open when said container is pushed downwardly in the barrel allowing liquid to pass from said barrel, through said lower opening and into said container; and
filtration means located at the lower end of said container for permitting the passage of soluble components of said blood specimen from said barrel to said container, but preventing passage of insoluble components when the container is pushed into the barrel with said upper opening of said container open.

14. A method for separating and isolating the lighter components of a blood specimen from its heavier components comprising the steps of:
providing a device having a barrel with an upper opening and means for selectively introducing said blood specimen, using a needle through a lower end of said barrel, said introducing means comprising a piercable membrane, a container acting as a fluid plunger slidable within said barrel between upper and lower positions, said container including a lower opening and an upper opening, one-way valve means disposed on said lower opening of said container between said container and said barrel for controlling fluid flow therebetween, said valve means operating in response to the direction of container movement within said barrel wherein upward container movement opens said valve and downward container movement closes said valve, and filter means disposed immediately above said one-way valve means within said fluid flow;

lifting said container within said barrel such that said valve means closes, thereby creating a vacuum within said barrel;

using said created vacuum within said barrel to draw in said blood specimen from a blood source;

removing said needle from said membrane;

centrifuging said barrel such that said container blood specimen separates into lighter and heavier fluid components, said lighter fluid components being located closer to said container than said heavier components;

lowering said container into said lighter fluid components such that said valve means opens and said lighter fluid components flow past said filter means into said container; and lifting said container such that said valve means closes, thereby isolating said lighter components from said heavier components.

* * * * *